(12) United States Patent
de Avila e Silva et al.

(10) Patent No.: US 8,762,119 B2
(45) Date of Patent: Jun. 24, 2014

(54) METHOD, SYSTEM AND APPARATUS TO PREDICT AND/OR RECOGNIZE AND/OR CLASSIFY BIOLOGICAL SEQUENCES

(75) Inventors: Scheila de Avila e Silva, Caxias do Sul (BR); Sergio Echeverrigaray Laguna, Caxias do Sul (BR); Gunther Johannes Lewezuk Gerhardt, Porto Alegre (BR)

(73) Assignee: Universidade de Caxias do Sul, Caxias do Sul (BR)

( * ) Notice: Subject to any disclaimer, the term of this patent is extended or adjusted under 35 U.S.C. 154(b) by 220 days.

(21) Appl. No.: 12/855,366

(22) Filed: Aug. 12, 2010

(65) Prior Publication Data

US 2013/0073216 A1    Mar. 21, 2013

(51) Int. Cl.
| | | |
|---|---|---|
| G06G 7/58 | (2006.01) | |
| G06F 7/60 | (2006.01) | |
| G01N 33/48 | (2006.01) | |
| G01N 33/50 | (2006.01) | |
| G01N 31/00 | (2006.01) | |
| G06F 19/24 | (2011.01) | |
| G06F 19/12 | (2011.01) | |
| G06F 19/22 | (2011.01) | |

(52) U.S. Cl.
CPC ............... *G06F 19/24* (2013.01); *G06F 19/12* (2013.01); *G06F 19/22* (2013.01)
USPC ........ 703/11; 703/2; 702/19; 702/20; 702/22; 702/27

(58) Field of Classification Search
None
See application file for complete search history.

(56) References Cited

PUBLICATIONS

Gerhardt et al. Network clustering coefficient approach to DNA sequence analysis. Chaos, Solitons and Fractals, 2006, vol. 28, pp. 1037-1045.*
Andrews et al. Survey and critique of techniques for extracting rules from trained artificial neural networks. Knowledge-Based Systems, vol. 87, 1995, pp. 373-389.*
Borukhov et al. RNA polymerase holoenzyme: structure, function, and biological implications. Current Opinion in Microbiology, 2003, vol. 6, pp. 93-100.*
Polat et al. A novel approach to estimation of *E. coli* promoter gene sequences: Combining feature selection and least square support vector machine (FS_LSSVM). Applied Mathematics and Computation, vol. 190, 2007, pp. 1574-1582.*

* cited by examiner

*Primary Examiner* — Russell S Negin
(74) *Attorney, Agent, or Firm* — Laurence P. Colton; Smith Risley Tempel Santos LLC (57) ABSTRACT

A method, a system and an apparatus for predicting and/or recognizing and/or classifying biological sequences, specially sequence families with binding site recognition motifs poorly conserved, comprising, advantageously, the use of neural networks rules; providing enhanced and more accurate results; and is preferably used when the biological sequence is a promoter.

15 Claims, 3 Drawing Sheets

METHOD, SYSTEM AND APPARATUS TO PREDICT AND/OR RECOGNIZE AND/OR CLASSIFY BIOLOGICAL SEQUENCES

SEQUENCE LISTING

The instant application contains a Sequence Listing which has been submitted in ASCII format via EFS-Web and is hereby incorporated by reference in its entirety. Said ASCII copy, created on 28 Mar. 2011, is named 49954002.txt and is 1,943 bytes in size.

BACKGROUND OF THE INVENTION

1. Field of the Invention

The present invention is in the fields of bioinformatics and molecular biology. More specifically, the invention provides a method, a system and an apparatus to predict and/or recognize and/or classify biological sequences, especially binding site recognition motifs poorly conserved, comprising the use of rules extracted from neural networks learning process. The invention is particularly useful for the prediction, recognition and/or classification of promoters.

2. Prior Art

Promoter prediction and recognition in silico is a crucial open issue in molecular biology and a challenge in bioinformatics. Promoters are cis-acting elements located before the transcription start site (TSS) of the Open Reading Frame (ORF). Gene expression begins with the recognition of the promoter by RNA polymerase enzyme (RNAP). In bacteria, RNAP holoenzyme consists of five subunits ($2\alpha$, $\beta$, $\beta'$, $\omega$) and an additional sigma ($\sigma$) subunit factor (Borukov and Nudler, 2003; Thiyagarajan, et. al, 2005). The $\sigma$ subunit of RNAP is a key regulator of bacterial gene expression because it is responsible for the specific interaction of RNAP at the promoter region. The $\sigma$ factors control transcription initiation by directing RNAP binding to specific promoter sequences and "melting" the double-stranded DNA, thus the transcription of a given gene is dependent upon the $\sigma$ associated to the RNAP (Doucleff, 2007; Borukhov and Nudler, 2003; Hook-Barnard, et. al 2006).

Bacterial cells use alternative $\sigma$ factors, specific for different subsets of promoters, in order to adapt to environmental changes (Borukhov and Nudler, 2003). *E. coli* has several $\sigma$ factors, the most prevalent of which are: $\sigma24$, $\sigma28$, $\sigma32$, $\sigma38$, $\sigma54$ and $\sigma70$ (the number indicates their molecular weight). Each $\sigma$ family has a role in the bacterial response to environmental conditions and it recognizes different consensual promoter sequence. For example, $\sigma32$ has a role in heat shock response, $\sigma28$ is associated to expression of flagellar genes during normal growth and $\sigma70$ is the major factor responsible for the bulk of transcription activity in the cell (Lewin 2008; Borukov and Nudler, 2003). Despite the family, all promoters have two important binding sites for RNAP, the −35 and −10 region relative to TSS nucleotide. These motifs are poorly conserved, particularly among $\sigma$ families. The canonical consensus for −35 and −10 regions and the number of nucleotides between them are (Lewin, 2008):

$\sigma32$—CCCTTGAA 13-15 pb CCCGATNT (SEQ ID NO: 1)
$\sigma28$—CTAAA 15 pb GCCGATAA (SEQ ID NO: 2)
$\sigma70$—TTGACA 16-18 bp TATAAT (SEQ ID NO: 3)
$\sigma54$—CTGGNA 6-bp TTGCA (SEQ ID NO: 4)

The consensual motifs recognized by $\sigma24$ and $\sigma38$ has not been described, due to their low conservation or reduced number of promoters confirmed.

The variation among consensus sequences recognized by each $\sigma$ factor, particularly the relative position of the conserved motifs, limits the efficiency of a global analysis approach. The promoter prediction should be done for each $\sigma$ family separately, since the analysis of a given promoter by comparison with $\sigma70$ promoter consensual motif can led to incorrect result.

Promoter compilations and analysis allowed the development of computer programs which predict the location of promoter sequences on the basis of its homology using consensus sequences or a reference list of promoters (Polat and Günes, 2007). The classical approach for promoters prediction involves the development of algorithms that used position weight matrices (PWMs). This methodology gives results by aligning examples of sequences and estimating the base preference at each position of a matrix (Gordon et al, 2006; Stormo, 2000; Hannenhalli and Wang, 2005).

In the last years, Machine Learning approaches have been applied for promoter recognition and prediction. Among these, Support Vector Machines (SVM), and Neural Network (NN) gave promising results. The SVM methods use a training algorithm and can represent complex nonlinear functions. This algorithm aims to separate the data set into two classes by a hyperplane (Kapetanovich et. al, 2004). The SVM can be applied to identify important biological elements: transcription factors (Holloway, 2007), promoters (Polat and Gunes, 2007; Liang and Li, 2006), transcription start sites (Gordon et. al, 2006; Gao, T., et al, 2009), among others.

The NNs are computational tool with complex nonlinear functions. They have been used for many biologic applications, as promoter prediction (Demeler and Zhou, 1991; Burden et. al, 2005; Rani et. al, 2007), gene expression (Tan and Pan, 2005; Janga and Collado-Vides, 2007) and protein analysis (HellesFonseca, 2009; Chae et. al, 2009). The NNs are adequate for promoter prediction and recognition due to their ability to identify degenerated, imprecise and incomplete patterns merged in those sequences, and achieved high performance when processing large genome sequences (Cotik et. al, 2005; Kalate et. al, 2003). Moreover, the NN methodology allows rule extraction from trained networks, which can assist in uncovering of biologic rules learned from the input data (Andrews et. al, 1995).

In literature, there are some papers describing promoter predictors, as BDGP (Reese M G, 2001), however none of them uses the rules extracted from neural network training cited herein, as following described.

Some patent related documents describe prediction tools using biological information, as following described.

Document US 2010/0057419 describes a fold-wise classification of proteins comprising the prediction of a fold pattern of a protein of interest having an unknown fold pattern by training a system to correlate structural or sequence features to the known protein fold pattern to predict protein fold patterns, preferably using SVMs. The present invention describes the use of neural network (NN) rules to classify, predict and/or recognize bacterial biological sequences poorly conserved, which is not cited in the above document, and do not include the specific prediction of protein fold patterns.

Document US 2009/0111099 describes a method for promoter detection and analysis comprising the insertion of a sequence candidate into a vector comprising a TAG sequence. The present invention describes the use of neural network (NN) rules to classify, predict and/or recognize bacterial biological sequences poorly conserved, which is not cited in the above document.

Document US 2008/0147369 describes methods, systems and software for identifying functional biomolecules comprising the generation of a model through the identification of cross-product terms using genetic algorithms. The present invention describes the use of neural network (NN) rules to classify, predict and/or recognize bacterial biological sequences poorly conserved, which is not cited in the above document.

Document WO 2007/059119 describes systems and methods for identifying diagnostic indicators using neural network rules, determining responsiveness to a therapy. The present invention is related to the use of neural network rules to classify, predict and/or recognize bacterial biological sequences poorly conserved, which is not described in any previous document, and do not is applied to identification of diagnostic indicators.

In view of the prior art cited above, it can be seen that no relevant prior art disclosing a mathematical approach to validate protein mutations as disclosed herein was found.

Objects and advantages of the invention set forth herein and will also be readily appreciated here from, or may be learned by practice with the invention. These objects and advantages are realized and obtained by means of instrumentalities and combinations pointed out in the specification and claims.

BRIEF SUMMARY OF THE INVENTION

In a first aspect, the present invention provides a method, system and apparatus to biological prediction, using nonlinear interactions between functional modules inside new and inventive bioinformatics tools, used herein to predict biological features, especially bacterial biological sequences poorly conserved, as promoters.

Therefore, it is an object of the present invention to provide a method, system and/or apparatus to predict and/or recognize and/or classify binding site recognition motifs poorly conserved, comprising the use of neural networks rules for multiple biological sequences poorly conserved, being the biological sequence preferably a promoter.

It is an object of the present invention to provide a method, system and apparatus to predict and/or recognize and/or classify biological sequences, especially sequence families with binding site recognition motifs poorly conserved, comprising the use of neural networks rules. In a preferred embodiment, the invention provides for a bacterial promoter prediction tool, denoted heretofore as BacPP. Differently of other prediction tools, which employ only σ70 sequences for the prediction of all promoters, BacPP is based on rules extracted from NN learning process for σ24, σ28, σ32, σ38, σ54 and σ70 promoter family. The information obtained from the rules was weighted to maximized promoters prediction and classification according with their σ factor.

It is an object of the present invention a method to predict biological features comprising:

a) NN learning for "X" binding site recognition motifs poorly conserved;
b) rule extraction for "X" binding site recognition motifs poorly conserved;
c) replace of prototype values from NN rule extraction by an integer number for "X" binding site recognition motifs poorly conserved;
d) analysis of the sequences for "X" binding site recognition motifs poorly conserved;
e) sequence score (>cut-off value);
f) verify if it is a promoter of "X" sigma factor family,
where X means the family of a given sequence.

Preferably, the binding site recognition motifs poorly conserved are bacterial promoters, belong to different σ factor. More preferably, the σ factor comprises σ24, σ28, σ32, σ38, σ54 and σ70.

It is also an object of the present invention a system comprising the method to predict bacterial biological features described above.

It is also an object of the present invention an apparatus comprising the method to predict bacterial biological features described above.

These and other objects of the invention will become more evident to the skilled persons by the reading of the detailed description below.

DETAILED DESCRIPTION OF PREFERRED EMBODIMENTS

All the examples shown in the present application are to be understood only as illustrative examples, and not to limit the scope of the invention. All the examples disclosed herein as well as similar or equivalents ways to achieve the objects of the invention are to be encompassed by the present invention.

Method, System, Apparatus to Predict/Recognize/Classify Biological Sequences

It is an object of the present invention a method, system and/or apparatus to predict and/or recognize and/or classify biological sequences, specially binding site recognition motifs poorly conserved, comprising the use of neural networks rules for bacterial biological sequences poorly conserved, being the biological sequence preferably a promoter.

It is also an object of the present invention a system comprising the method to predict biological features described above.

Preferably, the system can be understood as, but not limited to, any software and/or middleware comprising the method previously described.

It is also an object of the present invention an apparatus comprising the method to predict biological features described above.

Preferably, the apparatus can be understood as, but not limited to, any hardware or computer comprising the method to predict bacterial biological features described above.

It is an object of the present invention a method to predict and/or recognize and/or classify bacterial biological features comprising:

a) NN learning for "X" binding site recognition motifs poorly conserved;
b) rule extraction for "X" binding site recognition motifs poorly conserved;
c) replace of prototype values from NN rule extraction by an integer number for "X" binding site recognition motifs poorly conserved;
d) analysis of the sequences for "X" binding site recognition motifs poorly conserved;
e) sequence score (>cut-off value);
f) verify if it is a promoter of "X" sigma factor family,
where X means the family of a given sequence.

Binding Site Recognition Motifs Poorly Conserved

The binding site recognition motifs poorly conserved of the present invention comprise any biological sequence (DNAs, RNAs, protein sequences, among others) with motifs poorly conserved capable of recognize any biological and/or chemical binding site. Preferably, the binding site recognition motifs poorly conserved and/or biological sequences poorly conserved are promoters, more preferably promoters. In a preferred embodiment, the σ factors comprise σ24, σ28, σ32, σ38, σ54 and σ70.

Preferably, the binding sites recognized by motifs poorly conserved and/or biological sequences poorly conserved are binding sites for RNAP, the −35 and −10 region relative to TSS nucleotide.

The binding site recognition motifs poorly conserved and/or biological sequences poorly conserved can be simultaneously used to train the NN network and, after obtained the NN rules, they can also be used as a target to be predicted/classified/recognized in biological sequences.

EXAMPLE 1

BacPP: Bacterial Promoter Prediction—A Tool to Promoter Prediction and Recognition Methods 1.1 Data Set

*Escherichia coli* promoter sequences obtained from RegulonDB database (Gama-Castro et. al, 2008), in its version available on April, 2009, were used as positive examples for NN training. A total of 1034 sequences, subdivided according to their σ factor were employed (Table 1). As negative examples for NN training random sequences with a probability of 0.28 for nucleotides adenine (A) and timine (T) and a probability of 0.22 for nucleotides cytosine (C) and guanine (G) were generated. The same numbers of positive and negative examples were used in the simulations carried out.

TABLE 1

Number of sequences employed in the simulation for each σ factor.

| σ factor | Number of promoter sequences |
|---|---|
| σ24 | 69 |
| σ28 | 21 |
| σ32 | 71 |
| σ38 | 99 |
| σ54 | 38 |
| σ70 | 740 |

Promoter sequences of others Enterobacteriaceae were obtained from available literature since the only web databases available are for *E. coli* and *Bacillus subtilis*. Thus, a total of 82 sequences belonging to *Citrobacter, Enterobacter, Klebsiella, Proteus, Salmonella, Shigella, Yersinia* genera were obtained and employed (Aldridge et. al, 2006; Beach and Osuna, 1998; Castellanos et al, 2009; Ging and Inoye, 1986; Hu et al, 2000; Ibanez-Ruiz et. al, 2000; Kutsukake et. al, 1990; Mares et. al, 1992; Maxson and Darwin, 2006; Penfound and Foster, 1999; Perez and Groisman, 2009; Ramirez-Santos et al, 2001; Skovierova et al, 2006; Smith and Somerville, 1997; Sulavik et. al, 1997; Toru et al, 1993; Yang et. al, 2008; Wösten and Groisman, 1999).

1.2 Neural Network Simulation

NN simulations were accomplished for each σ family. The nucleotides were encoded using a set of four binary digits as given by (Brunak et al, 1991): A=0100, T=1000, C=0001 e G=0010. An input sequence was classified as presumptive promoter if its output lay value was between 0.5 and 1.0. Otherwise, it was considered as a non-promoter.

The simulations were carried out in the R Environment (R Development Core Team, 2008). We chose back-propagation (BP) algorithm with a k-fold-cross validation. This choice was done in order to obtain statistically valid results. In this technique the dataset was divided into k subsets. At each iteration, one of the k subsets was used as the test set and the others were put together to form a training set. So the average error across all k trials was computed (Polat and Gunes, 2007). In the presented study the k values, determined by the number of promoter sequences available, were: 10 for σ70 promoters; 2 for σ28 and σ54 promoters; 3 for σ24, σ32 and σ38 promoters. These numbers for k value were determined by the number of available promoter sequences.

The results were evaluated comparing their: accuracy (A), specificity (S) and sensitivity (SN). These parameters were calculated using the following formulas:

$$A = \frac{TP + TN}{TN + TP + FN + FP} \quad \text{(Formula 1)}$$

$$S = \frac{TN}{TN + FP} \quad \text{(Formula 2)}$$

$$SN = \frac{TP}{TP + FN} \quad \text{(Formula 3)}$$

where, TP (true positive) are promoter sequences classified as promoter; TN (true negative) are random sequences recognized as non-promoters; FP (false positive) are random sequences classified as promoter and FN (false negative) are promoters classified as non-promoter sequences.

The NN is applicable in a variety of problems, but the learning process is complex (Andrews et. al, 1995). How NN learns to classify a given sequence as promoter or non-promoter can be understood by the rules extraction. Thus, an explanation of how each NN decision is made increase the knowledge about these sequences (Odajima et. al, 2008). In this specification, we extracted the rules based on the value of the hidden neurons by a methodology denoted FAGNIS, according to (Cechin, 1998). The rule extraction was developed out in the R Environment. This technique consists in segmenting a sigmoid function in three regions (see FIG. 1). For each input, it is verified in what region of the sigmoid the hidden neurons were fit. The maximum number of combinations is $3^n$, where n is a number of neurons in the hidden layer. Nevertheless, all the possible combinations do not occur and, only the more frequent combinations are considered. These combinations are the best representation of the input data. Therefore, the results are conveniently presented by a rule prototype, which we defined as average model of input data set. The rule can be written as a linear equation: "If x= or ~prototype then y=constant of linear equation+(coefficients of the linear equation)". Here, x is an input example, y corresponds to NN output and the coefficients of the linear equation are the nucleotides of the sequence.

1.3 BacPP Implementation

The BacPP tool was implemented in Python programming language (van Rossum, 2010). An overview of this approach is given in FIG. 1. The global idea of this tool was weighting the score obtained by NN prototypes rules extraction for each σ factor promoters, and uses these as models to determine and to classify promoters by their sigma family. Several weights were evaluated. The weights were defined using integer numbers between −10 and +10. For a given nucleotide, if the prototype score lied above 0.3 or 0.2, the values were replaced by a positive or negative number, respectively. If the prototype score lied between at 0.29 and 0.2, these prototype values were replaced by zero. The best weights are presented in the Table 2.

TABLE 2

The best weighting set to BacPP classification results

| Score from NN rule prototype | Integer number replacing it |
|---|---|
| Uppon 0.6 | +6 |
| 0.5 to 0.59 | +4 |
| 0.4 to 0.49 | +2 |
| 0.3 to 0.39 | +1 |
| 0.2 to 0.29 | 0 |
| 0.1 to 0.19 | −1 |
| Lower 0.1 | −3 |

Results

In the NN simulation, the architecture that best classified the input set of sequences for each σ promoter is presented on Table 3. A greater number of neuron in the hidden layer did not increase significantly the accuracy, the specificity or the sensitivity.

TABLE 3

The best architecture for every σ factor family simulation

| σ factor | Number of neurons in input layer | Number of neurons in hidden layer | Number of neurons in output layer |
|---|---|---|---|
| σ24 | 324 | 4 | 1 |
| σ28 | 324 | 2 | 1 |
| σ32 | 324 | 2 | 1 |
| σ38 | 324 | 2 | 1 |
| σ54 | 324 | 2 | 1 |
| σ70 | 324 | 5 | 1 |

Using the best architecture for each σ factor family, the NN achieved an average accuracy of 71.67%, a specificity of 71.08%, and a sensitivity of 72.98%, with low variation among σ factors (Table 4). The similarity between the specificity and sensitivity values within each σ, is an indicative of the consistence of the NN learning process. The accuracy, specificity and sensitivity values obtained for σ70 are lower but comparable with those previously reported using NN methodologies (Burden et al., 2005).

TABLE 4

Comparison among accuracy, specificity and sensitivity among σ factors

| Sigma factor | Accuracy (%) | Specificity (%) | Sensitivity (%) |
|---|---|---|---|
| σ 24 | 71.6 | 69.1 | 73.9 |
| σ 28 | 70.2 | 66.6 | 73.8 |
| σ 32 | 72.4 | 72.4 | 72.4 |
| σ 38 | 67.7 | 68.5 | 66.8 |
| σ 54 | 73.5 | 73.2 | 73.8 |
| σ 70 | 77.0 | 76.7 | 77.2 |

Figure 1:
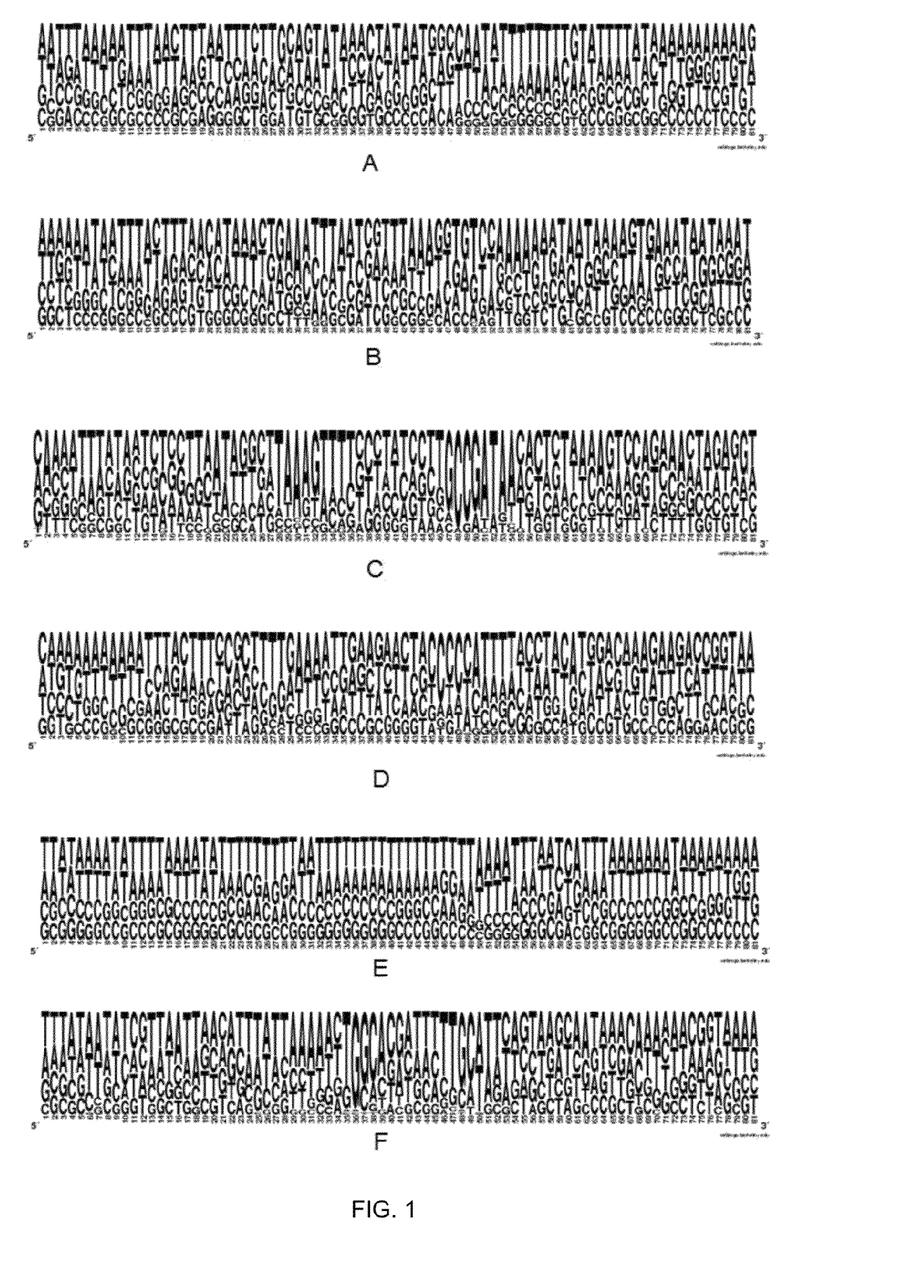
FIG. 1 shows the WebLogo Frequency Plot to NN prototypes for: A) σ24 promoters; B) σ28 promoters; C) σ32 promoters; D) σ38 promoters; E) σ54 promoters; and F) σ70 promoters.
Figure 2:
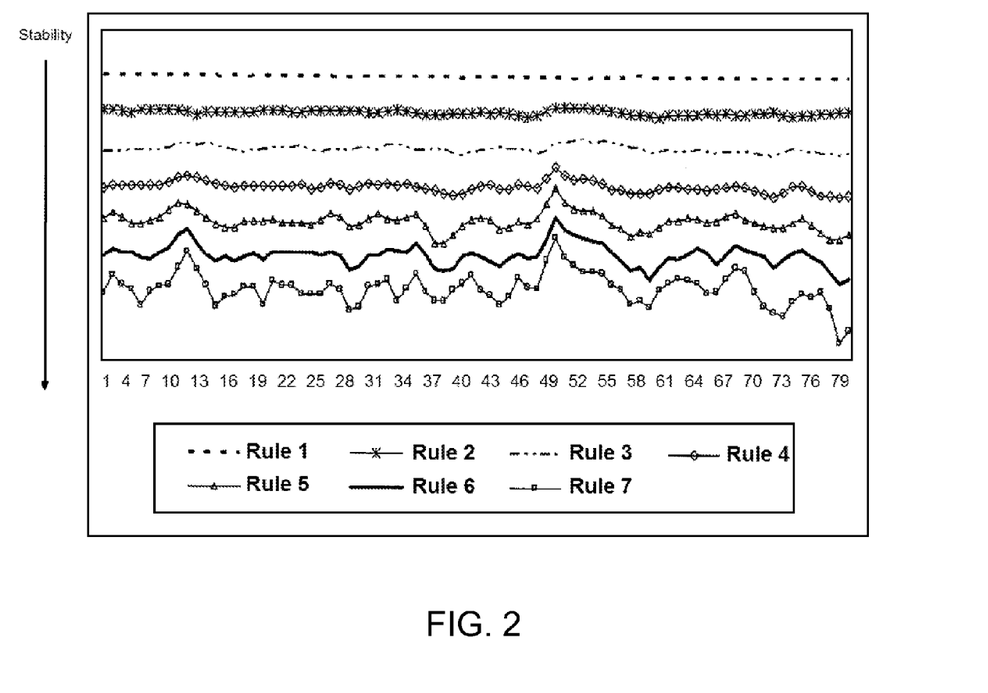
FIG. 2 shows the respective stabilities when different rules are applied (rules 1-7).

The NN prototypes, extracted from the trained NN using FAGNIS algorithm, for each σ factor family are shown as a frequency plot (Logo in FIG. 1).

Figure 3:
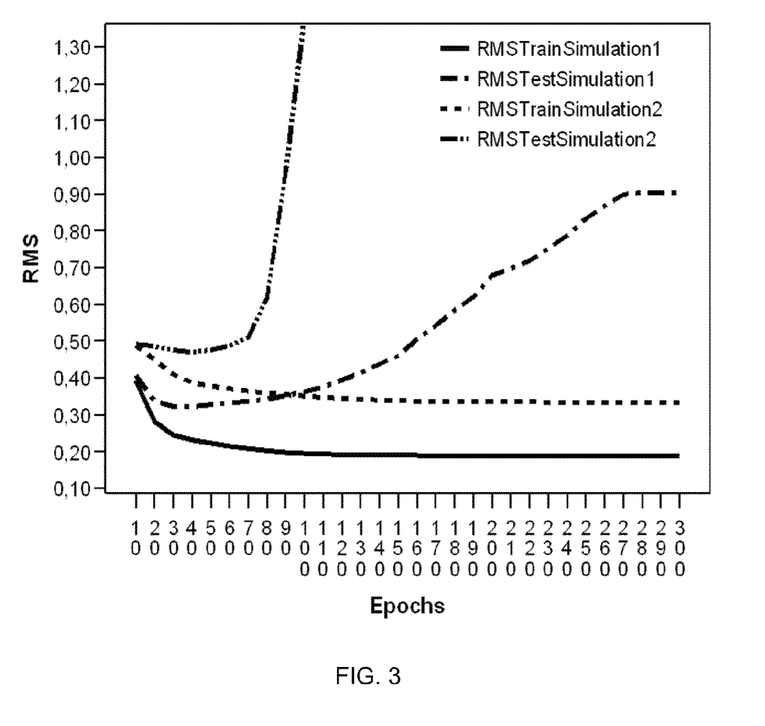
FIG. 3 shows the RMS in train and test simulations 1 and 2.

The prototype obtained for σ24 did not showed any highly conserved motif, but as most promoters, it is characterized by a high prevalence of AT nucleotides (Lewin, 2008). Until the moment, no conserved motifs have been described for σ24 promoter sequences. Conversely, σ28 promoter's prototype (FIG. 3) exhibited two conserved motifs, one between −15 and −7, TGCCGATAA, and an other between −33 and −25, TAAAGTTT, that match those previously described (Song at al., 2007).

The prototype obtained for the σ32 promoters was characterized by the presence of two partially conserved motifs. A −7 to −15 motif with a consensual sequence CYCYAW-WWW, and a −28 to −35 YTKRWWW sequence. According to IUPAC code, the letters Y, W, K, R represents: C or T, A or T, G or T, A or G, respectively. These motifs are similar to those described by Wang and deHaseth (2003). On the other hand, no typical conserve motifs were evidenced on σ38 promoters. However, a W-rich region could be identified in the first 11 nucleotides, with a T highly conserved at −7. Low conservation and W-rich motifs on σ38 promoters were evidenced by Typas et al. (2007).

The prototype obtained for σ54 promoters showed two conserved motifs: (1) a consensus sequence WWCGTT between −10 and −15, and (2) a ACGGT sequence between −22 and −26. These motifs are similar to those described by Barrios et al. (1999). σ70 promoters prototype was characterized by a high A/T/W content (88%) compared with the other promoters, which varied between 30% (σ32) and 58% (σ38). High AA, AT and TT dinucleotide frequency was reported by Kanhere and Bansal (2005) on E. coli σ70 promoters. However, the typical −10 and −35 conserved motifs were not evident on the prototype extracted from the NN. This fact may be due to the variation on the number of nucleotides between the +1 and the first motif, as well as between motifs on σ70 promoters (Shultzaberger et al., 2006).

In general, the prototype rules extracted from the NN showed the conserved motifs previously described for each σ family, indicating that the NN learning has biological foundation.

Considering the efficiency of the NN learning, the rules were ponderated and used to develop a prediction tool for bacterial promoter sequences, separated by σ family. This program was named BacPP.

As can be observed in Table 5, BacPP showed higher accuracy, specificity and sensitivity than the original NN. Using BacPP, the highest accuracies were obtained for σ54, σ28 and σ32, all above 90%. These σ family promoters exhibited highly conserved motifs, fact that can explain the efficiency of the prediction. Conversely, the lowest accuracy was obtained for σ70, the less conserved σ promoters. Although the σ70 promoters are the most abundant in bacterial genomes, they have more deviations from the canonical consensus promoters (Janga and Collado-Villes, 2007).

TABLE 5

The best architecture for every σ factor family simulation

| | Accuracy (%) | | Specificity (%) | | Sensitivity (%) | |
|---|---|---|---|---|---|---|
| σ factor | BacPP | NNPP | BacPP | NNPP | BacPP | NNPP |
| σ 24 | 86.9 | 67.2 | 95.6 | 60.8 | 78.2 | 50.7 |
| σ 28 | 92.8 | 68.2 | 90.4 | 75 | 95.2 | 50 |
| σ 32 | 91.5 | 68.4 | 92.9 | 60.5 | 90.1 | 64.7 |
| σ 38 | 89.3 | 68.2 | 83 | 62.6 | 93.9 | 64.6 |
| σ 54 | 97 | 67.8 | 100 | 60 | 94.11 | 48.5 |
| σ 70 | 83.6 | 74.4 | 85.4 | 68.7 | 81.8 | 80 |

To evaluate the efficiency of BacPP, the same set of promoters and random sequences were used for promoters prediction using BacPP and NNPP (Burden et al., 2005), another machine learning based algorithm. As can be observed in Table 5, BacPP showed higher accuracy, specificity and sensitivity, with values in the order of 90% and 65%, for BacPP and NNPP, respectively. All the parameters were higher even for σ70 promoters, used in NNPP modeling.

In other simulation, BacPP was used in a cross-test to evaluate the specificity of promoters classification by σ factor. For example, BacPP for σ70 (tester) was used against σ24, σ28, σ32, σ38 and σ54 promoter sequences (tested). In all cases, the highest of specificity was obtained for the own σ factor, indicating that BacPP efficiently classify promoter sequences by σ family. However, the values obtained when a given σ factor model was applied on other sigma sequences were higher than those obtained using random sequences, indicating there are some conservation among promoter sequences independent of the σ factor. This fact explains the relative efficiency of prediction models based on σ70 in the identification of other sigma sequences (Gordon et al., 2003; Burden et al., 2005).

A comparison of BacPP with previously reported machine learning based programs showed that BacPP average accuracy (90.2%), specificity (91.0%) and sensitivity (89.5%) are comparable with the most efficient approaches published until this moment. Oppon (2000) reported a neural network promoter prediction program (NNPP) that exhibited 60% specificity and 50% sensitivity for σ70 promoters. This program was further improved in its specificity (Burden et al., 2005). A SVM based approach using Sequence Alignment Kernel obtained an accuracy of 84%, specificity of 84% and sensitivity of 82% (Gordon et al., 2003). Polate and Günes (2007), with a least square support vector machines but using just 56 sequences obtained an accuracy of 84.6%, sensitivity of 90.9% and specificity of 80%.

NN methodology using dinucleotide information as input data achieved an accuracy of 96%, specificity of 98% and sensitivity of 93% for σ70 promoters using negative examples with 60% of AT nucleotides (Rani et al., 2007). Although highly efficient this approach is specific just for AT-rich sigma sequences like σ70. In other work, Rangannan and Bansal (2007) used DNA stability to predict promoter sequences and obtain an accuracy of just 52.2% with sensitivity of 98%.

When evaluated against a set of 82 promoter sequences of other enterobacterial species, BacPP exhibited an accuracy of 80.5%, with 86% sensitivity and 75% specificity, indicating that BacPP can be efficiently used for promoters prediction and classification in different Gram-negative bacteria.

In this invention, we present a novel approach for biological sequence prediction and classification based on weighting of the promoter prototype obtained from the rules extracted from NNs, as previously described. By separating the promoter sequences according its σ factor, we have demonstrated that the prediction and the knowledge about the promoters can be improved. The accuracies obtained for σ24, σ28, σ32, σ38, σ54 and σ70 *E. coli* promoters were 86.9%, 92.8%, 91.5%, 87.8%, 97.0% and 83.6%, respectively. When applied to a set of promoters from different enterobacteria, the accuracy of BacPP was 76%, indicating that this method can be expanded to other bacterial species. Differently from previous tools/methods described in the literature, BacPP allows not only the identification of bacterial promoters, but also their classification according with their σ factor. Those skilled in the art will readily appreciate the invention, and will understand that other embodiments are to be deemed as within the scope of the invention and of the appended claims.

---

What is claimed is:

1. A method to predict and/or recognize and/or classify biological sequences wherein said biological sequences are predicted, recognized and/or classified by rules extracted from Neural Network (NN) learning process for poorly conserved biological sequences, the process being carried out by a computer and comprising the steps of:
   a) conducting NN learning for "X" sequences obtained from a database of sequences of binding site recognition motifs poorly conserved, namely, sequences where the relative position of the motifs are poorly conserved;
   b) extracting a rule for the "X" sequences of binding site recognition motifs poorly conserved;
   c) replacing prototype values from NN rule extraction by an integer number for the "X" sequences of binding site recognition motifs poorly conserved;
   d) analyzing each of the sequences for the "X" sequences of binding site recognition motifs poorly conserved;
   e) scoring each of the sequences and determining whether each of the sequences is greater than a cut-off value; and
   f) verifying if each of the sequences is a promoter of "X" sigma factor family,
   where "X" means the family of a given sequence, "X" being more than 1, and
   wherein the architecture of the NN learning process comprises between 2 and 5 neurons in a hidden layer of the NN,
   thereby allowing for the predicting and/or recognizing and/or classifying of the sequence.

2. The method according to claim 1, wherein the poorly conserved binding site recognition motifs are sequences related to the promoters.

3. The method according to claim 1, wherein the consensual binding site recognition motifs belong to the σ24, σ28, σ32, σ38, σ54, σ70 factors family.

4. The method according to claim 1, wherein the architecture of the NN learning process comprises around 324 neurons in the input layer.

5. The method according to claim 1, wherein the architecture of the NN learning process comprises around 1 neuron in the output layer.

6. The method according to claim 1, wherein a total of 1034 sequences related to σ factor are employed to train the NN.

7. The method according to claim 1, wherein the neural network simulations are accomplished for each family of sequences, considering as a promoter an output lay value between 0.5 and 1.0.

8. The method according to claim 1, using back-propagation algorithm with a k-fold-cross validation.

9. The method according to claim 1, wherein the rules are extracted using FAGNIS methodology.

10. The method according to claim 1, wherein a tool to promoter prediction and recognition is implemented, weighting the score obtained by the NN prototypes rules.

11. The method according to claim 10, wherein the tool is BacPP.

12. The method according to claim 1, wherein the weights are defined using integer numbers between −10 and +10.

13. The method according to claim 1, wherein the accuracy, specificity or sensitivity of NN is between 65-80%.

14. The method according to claim 1, wherein the accuracy, specificity and/or sensitivity is between 75-100%.

15. An apparatus to predict and/or recognize and/or classify biological sequences wherein said apparatus comprises means for the prediction, recognition and/or classification of biological sequences according to rules extracted from Neural Network (NN) learning process for poorly conserved biological sequences, comprising:
   a) means for NN learning for "X" sequences of binding site recognition motifs poorly conserved, namely, sequences where the relative position of the motifs are poorly conserved;
   b) means for rule extraction for "X" sequences of binding site recognition motifs poorly conserved;
   c) means for replacing prototype values from NN rule extraction by an integer number for "X" sequences of binding site recognition motifs poorly conserved;
   d) means for analyzing each of the sequences for "X" sequences of binding site recognition motifs poorly conserved;
   e) means for scoring each of the sequences and determining whether each of the sequences is greater than a cut-off value; and
   f) means for verifying if each of the sequences is a promoter of "X" sigma factor family,
   where "X" means the family of a given sequence, "X" being more than 1,
   wherein the architecture of the NN learning process comprises between 2 and 5 neurons in a hidden layer of the NN, and
   wherein the apparatus allows for the predicting and/or recognizing and/or classifying of the sequence.

* * * * *

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(23)
<223> OTHER INFORMATION: a, c, t, g, unknown or other
<220> FEATURE:
<221> NAME/KEY: misc_feature
<222> LOCATION: (9)..(23)
<223> OTHER INFORMATION: This region may encompass 13 to 15 nucleotides
<220> FEATURE:
<221> NAME/KEY: modified_base
<222> LOCATION: (30)..(30)
<223> OTHER INFORMATION: a, c, t, g, unknown or other

<400> SEQUENCE: 1
cccttgaann nnnnnnnnnn nnncccgatn t                                          31

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(20)
```

```
<223> OTHER INFORMATION: a, c, t, g, unknown or other

<400> SEQUENCE: 2
ctaaannnnn nnnnnnnnnn gccgataa                                              28

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(24)
<223> OTHER INFORMATION: a, c, t, g, unknown or other
<220> FEATURE:
<221> NAME/KEY: misc_feature
<222> LOCATION: (7)..(24)
<223> OTHER INFORMATION: This region may encompass 16 to 18 nucleotides

<400> SEQUENCE: 3
ttgacannnn nnnnnnnnnn nnnntataat                                            30

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(12)
<223> OTHER INFORMATION: a, c, t, g, unknown or other

<400> SEQUENCE: 4
ctggnannnn nnttgca                                                          17
```